United States Patent [19]
Santini

[11] Patent Number: 6,026,673
[45] Date of Patent: Feb. 22, 2000

[54] ELECTRONIC DEVICE FOR SENSING GAS PRESENT IN THE ENVIRONMENT

[75] Inventor: Ernesto Santini, Sozzago, Italy

[73] Assignee: Bticino S.P.A., Milan, Italy

[21] Appl. No.: 08/928,425

[22] Filed: Sep. 12, 1997

[30] Foreign Application Priority Data

Sep. 12, 1996 [IT] Italy .............................. MI96A 01873

[51] Int. Cl.[7] ................................................ G01N 27/00
[52] U.S. Cl. ........................... 73/1.06; 73/31.02; 702/100
[58] Field of Search ..................... 73/1.06, 1.07, 73/31.02, 23.21; 702/100

[56] References Cited

U.S. PATENT DOCUMENTS

| | | | |
|---|---|---|---|
| 3,812,330 | 5/1974 | Bowman et al. ..................... | 73/1.06 X |
| 4,481,804 | 11/1984 | Eberhardt et al. ....................... | 72/1.06 |
| 5,305,231 | 4/1994 | Coppler et al. . | |
| 5,502,659 | 3/1996 | Braster et al. ........................ | 73/1.06 X |
| 5,526,280 | 6/1996 | Consadori et al. .................. | 73/23.2 X |
| 5,659,125 | 8/1997 | Ernst ..................................... | 73/1.07 X |
| 5,672,806 | 9/1997 | Hung ....................................... | 73/1.06 |

FOREIGN PATENT DOCUMENTS

| | | |
|---|---|---|
| 0293255 | 11/1988 | European Pat. Off. . |
| 0345563 | 12/1989 | European Pat. Off. . |
| 2298285 | 8/1996 | United Kingdom . |

Primary Examiner—Thomas P. Noland
Attorney, Agent, or Firm—Pillsbury Madison & Sutro LLP

[57] ABSTRACT

An electronic device for sensing gas present in the environment, comprising a presence sensor for the gas concentration, a digital electronic circuit for processing data, a permanent random access memory, a bidirectional serial logic gate, at least one optical and/or acoustic warning device, and an electrical actuator or relay. During its production the electronic device receives from an external processor, via a serial line, data (gas concentration, temperature, humidity) relating to the environment in which the sensor is located, the data being analyzed by the digital electronic circuit together with the values present at the output of the sensor, for the purpose of calibrating the device.

7 Claims, 2 Drawing Sheets

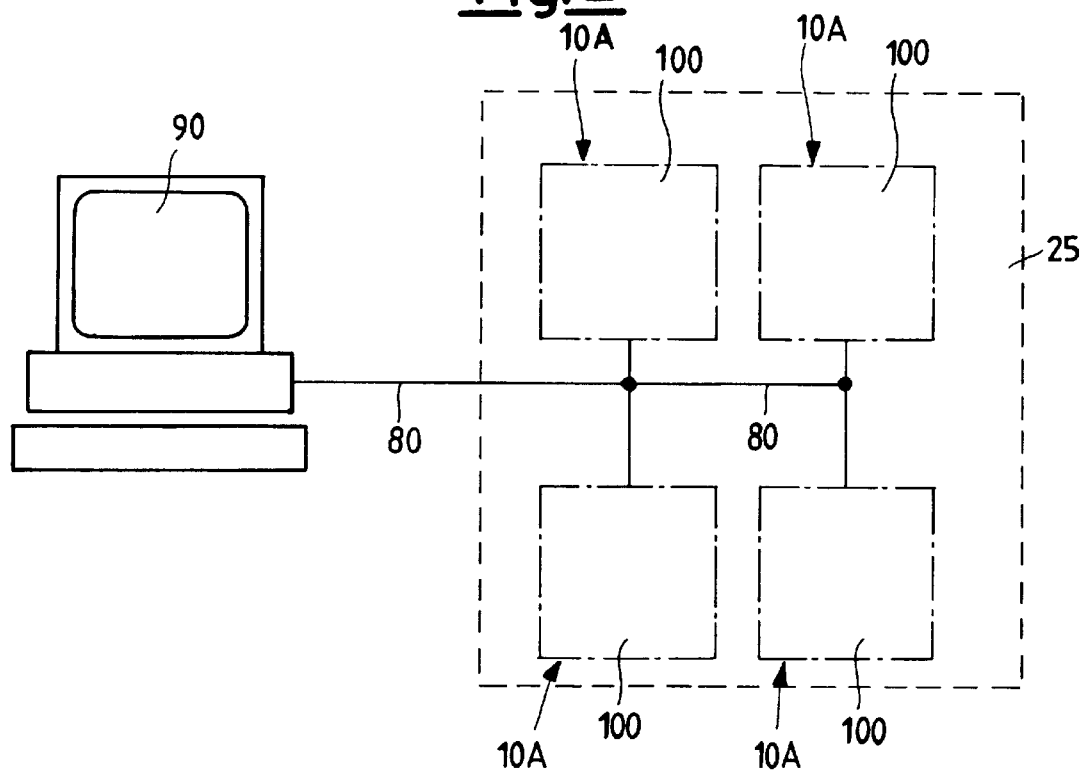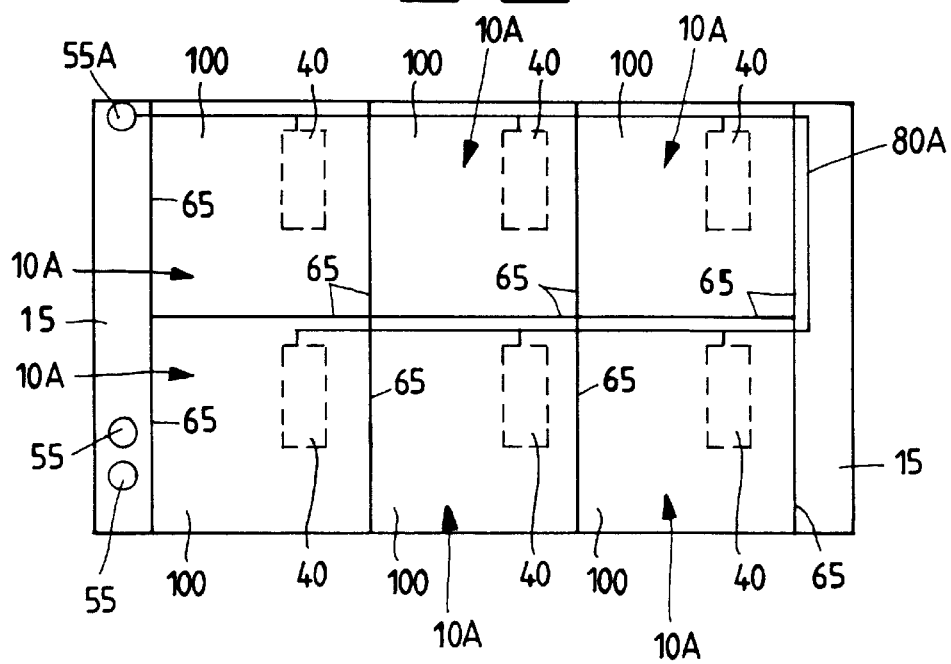

6,026,673

ELECTRONIC DEVICE FOR SENSING GAS PRESENT IN THE ENVIRONMENT

CROSS-REFERENCES TO RELATED APPLICATIONS

Not Applicable

STATEMENT REGARDING FEDERALLY SPONSORED RESEARCH OR DEVELOPMENT

Not applicable

BACKGROUND OF THE INVENTION

1. Field of the Invention

This invention relates to an electronic device for sensing gas present in the environment.

2. Description of the Related Art Including Information Disclosed Under 37 C.F.R. §§1.97 and 1.98

Numerous types of devices currently exist for sensing the presence of gas in environments. In particular, sensing devices for flammable gases such as methane or LPG for domestic use are very widespread. These devices generally consist of:

1) a gas presence sensor, usually based on semiconductor, catalytic or electrochemical technology, which provides as output an electrical signal proportional to the gas concentration in the air;
2) an electronic circuit for processing the output signal from the sensor (a threshold comparator or a digital processing logic circuit);
3) an electrical circuit for optical and/or acoustic alarm indication, which operates a buzzer or siren and/or lights a lamp or an LED light source.

Sometimes the device also comprises an electrical actuator circuit which acts on auxiliary members, such as solenoid valves for halting gas delivery, or comprises an electrical or electronic output circuit arranged to repeat the alarm indication at other supplementary indicator means.

However, devices of this type have numerous drawbacks, which it would be desirable to reduce or, better still, eliminate. In this respect, firstly during the production of such sensing devices, the sensors themselves are calibrated on the basis of the input/output specifications for the electronic signal processing components downstream of said sensors.

In this manner, the sensitivity and the threshold sensing level for the gas concentration in the environment, and declared on the data plate of the sensing devices produced, become standardized. Moreover, checking for possible faults (in the sense of phenomena which make it impossible to effect normal calibration) is carried out on a small number of devices at a time, as the fault indication is given independently by each sensing device. In addition, current national and international regulations on this subject, plus proper production procedures, both require an operational test to be carried out on all manufactured sensing devices in an environment in which a gas concentration equal to an operating threshold value is present.

It is apparent that, again in this case, the number of devices which can be checked is limited by the fact that each of them independently provides intervention and/or an alarm indication. According to known techniques, the device is often calibrated manually by operating a potentiometer or by selecting resistors with different resistance values, to be connected to the measurement sensor. Calibrating the device is therefore particularly delicate and critical and requires lengthy and costly manual operations, as the sensor has to be placed in environments of known gas concentration at controlled temperature.

Sometimes, when a digital processing circuit is provided, electronic calibration is carried out consisting of recording in a permanent memory the compensation factors for the values read by the sensor in the presence of the known gas concentration. However this operation is performed in an environment of known gas concentration and controlled temperature, and hence the calibration is dependent on the temperature of the atmosphere in which the gas is present, and to a certain extent it also depends on the percentage of moisture in the environment in which the device is installed. Finally, even in the case of electronic calibration the sensing devices must be calibrated one at a time. All this results in lengthy times for these operations, due also to the fact that the gas sensors require a stabilization time during calibration in a known atmosphere. Moreover the chambers containing measured gas must be washed periodically, the sensors must be preheated, and other costly and bulky production equipment has to be provided to ensure the necessary degree of compatibility between the measurements effected and the results awaited. Finally, possible operations involved in temperature-control or conditioning of the calibration and test environment have to be taken into account.

BRIEF SUMMARY OF THE INVENTION

An object of the present invention is therefore to indicate an electronic device able to sense gas present in the environment, which obviates the aforesaid drawbacks by enabling the sensor to be automatically calibrated on the basis of accurate measurements of gas concentration, temperature and humidity of the environment.

A further object of the present invention is to subject all the produced devices to simultaneous calibration and programming, while at the same time creating a map showing the location of possible faults (understood in the sense of the impossibility of carrying out normal calibration operations).

A further object of the invention is to indicate an electronic device for sensing gas present in the environment which is of simple and economical construction, without using costly components or complex techniques.

These and further objects are attained by an electronic device for sensing gas present in the environment in accordance with claim 1, to which reference should be made for brevity. Advantageously, the gas sensing device of the present invention is placed in an environment of known gas concentration during calibration.

From an external electronic processor the device receives, via a serial line and a bidirectional logic communication gate, a series of parameters relative to the environment in which it is located, such as the forced gas concentration in the environment, the gas concentration read on the sensor, the temperature and the humidity of the environment.

A digital electronic circuit analyzes this information to construct a table of values which represent the differences between the gas concentration value in air, which is read on the sensor, and the value expected on the basis of predetermined environmental temperature and humidity parameters, which are fed in from the outside by the operator.

The difference values are stored in a permanent electronic memory. Hence, during normal operation the sensing device is able to correct the gas concentration value read on the sensor by comparison with the calibration parameters memorized in the permanent memory, and to intervene for a predetermined exact threshold value.

BRIEF DESCRIPTION OF THE SEVERAL VIEWS OF THE DRAWINGS

Further objects and advantages of the present invention will be apparent from the ensuing description and from the accompanying drawings, which are provided by way of non-limiting example and on which:

FIG. 2 is a schematic block representation of a plurality of electronic gas sensing devices (specifically, four are shown), during sensor calibration, according to the present invention;

FIG. 3 is a block diagram of a plurality of electronic devices according to the invention (specifically, six are shown) formed on printed circuit cards, shown during sensor calibration. In the said FIG. 10A indicates overall the electronic device for sensing gas in the environment, according to the present invention.

DETAILED DESCRIPTION OF THE INVENTION

Figure 1:
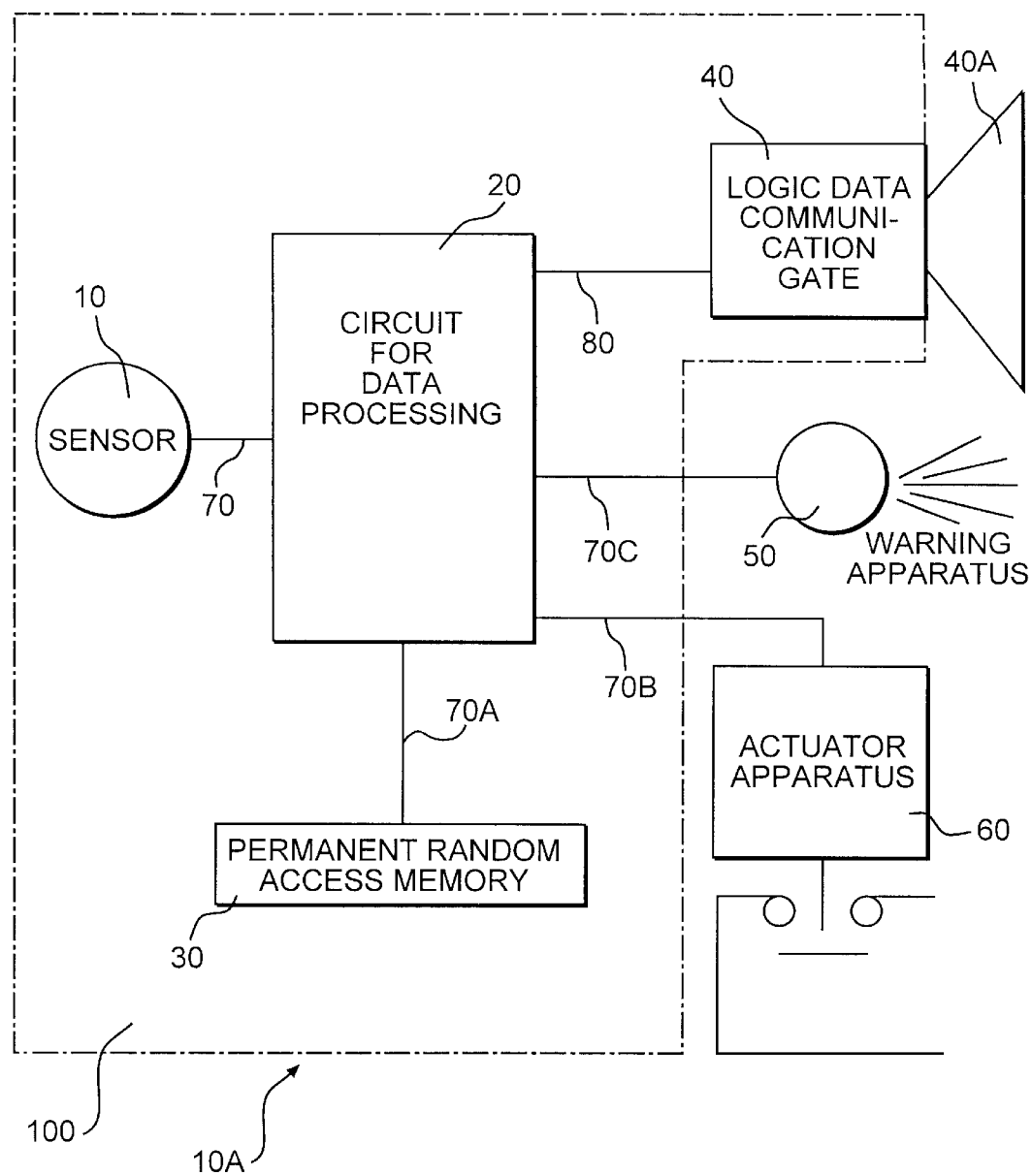
FIG. 1 is a block diagram of the electronic device for sensing gas present in the environment, according to the present invention, during normal operation.

The reference numeral 10 indicates a sensor for gas concentration measurement, 20 indicates a digital electronic circuit for data processing, 30 indicates a permanent random access memory, of EEPROM or FLASH EPROM type or the like, or of buffered RAM type, 40 indicates a logic data communication gate of bidirectional serial type, 50 indicates an optical and/or acoustic warning apparatus, and 60 indicates an actuator apparatus (for example a relay).

The reference numeral 70 indicates a communication line (or bus) for data originating from the sensor 10 and arriving at the electronic processing circuit 20, 70A indicates the line along which data pass from the electronic circuit 20 to the memory 30, 70B indicates the connection line between the electronic circuit 20 and the actuator apparatus 60, 70C indicates the connection line between the electronic circuit 20 and the warning apparatus 50, and 10B indicates a dashed line containing within it discrete electronic components, which can alternatively be integrated onto a printed circuit card 100.

The reference numeral 15 indicates the terminal strip of the printed circuit in question, 55 indicates generic external connection points, and 55A indicates a connection point to which all the serial logic gates 40 of the various electronic sensing devices 10A are connected by a single printed conductor 80A. Finally, 65 indicates the lines along which the printed circuit cards 100, on each of which each individual sensing device 10A is integrated, are separated.

The serial communication output, positioned in correspondence with the logic gate 40, is connected to the electronic circuit 20 by the bidirectional serial communication line 80 and can be controlled as an alarm indication output if an appropriate acoustic warning means 40A is provided.

Finally, 90 indicates an electronic processor external to the sensing device 10A, which during the calibration of the sensor 10 provides a table of parameters (gas concentration, temperature, humidity) relative to the environment 25 in which the sensing device 10A is located.

During its normal operation, the electronic device 10A for sensing gas in the environment, according to the present invention, senses the electrical signal present as output from the sensor 10 and, on the basis of the calibration parameters (gas concentration, ambient temperature, humidity) present in the permanent memory 30, decides whether or not to activate the logic communication gate 40 or the optical and/or acoustic warning devices/and/or the actuator apparatus 60, via the lines 80, 70C, 70B respectively.

Specifically, the serial output at the logic gate 40 can be controlled as output for an alarm state, by means of the acoustic warning device 40A.

In contrast, during the production of the sensing devices 10A, by externally forcing the serial communication line 80, at the moment in which it is powered, the electronic device 10A is put into the calibration state.

Located in an environment 25 in which the gas concentration is known, the sensing device 10A receives from an external processor 90, via a serial line 80, a table of parameters relative to the environment 25 in which it is located, and containing information related to the gas concentration set from the outside or read on the screen of the sensor 10, and the measured air temperature and humidity.

The electronic processing circuit 20 analyzes this information together with the gas concentration read on the sensor 10. In this manner it is able to construct a table containing the differences between the values read on the sensor 10 and the expected value for each predetermined individual gas concentration and for each individual environmental condition set from the outside by an operator (by feeding in the parameters relative to the air temperature and humidity). The table is stored in the permanent memory 30.

Under normal operating conditions the electronic circuit 20 is able to correct the value read on the sensor 10 by the calibration parameters which have been stored in the memory 30, such that the sensing device 10A acts (to operate the optical and/or acoustic warning device 40A, 50 and/or the actuator apparatus 60) at a desired threshold gas concentration.

From the aforegoing description the characteristics of the electronic sensing device of the present invention are apparent, as are its advantages.

In particular:

no manual calibration operations are required, and the environmental parameters (gas concentration, temperature, air humidity) can be roughly set by the external operator, but are read accurately by the external processor, which is connected to the serial line of the digital electronic circuit;

several sensing devices can be programmed simultaneously;

warning of a fault, in the sense of not being able to carry out the normal calibration operations, is indicated by dedicated devices via a serial line, at the same time enabling a fault location map to be formed for easy consultation by an external operator;

a final control test on the device can be carried out immediately after calibration, without removing the controlled atmosphere chamber, by simply scouring in air and blowing gas in at the desired concentration (indication can be via the serial line);

the calibration is substantially independent of the air temperature and humidity, in that compensation curves can be calculated for use simply with the environmental parameter values which have been measured.

It is apparent that numerous modifications can be made to the electronic sensing device of the present invention, but without leaving the novelty principles of the inventive idea, it also being apparent that in the practical implementation of the invention the materials, the shapes and the dimensions of the illustrated details can be chosen at will according to requirements, and that these can be replaced by others technically equivalent.

For example, a calibration operation analogous to the aforedescribed can also be implemented on electronic cards mounted on a printed circuit terminal strip but not yet separated from each other, and without the bulk of the containers. In this case a single printed conductor connects all the serial gates of the various electronic sensing devices to a single connection point external to the printed circuit terminal strip; the circuit is then separated, together with the detachment of the cards of each individual sensing device, along the connection lines.

This calibration technique on unseparated printed circuit cards allows high packing density of the sensing devices, with consequent productivity increase.

I claim:

1. An electronic device for sensing gas present in an environment, comprising:
   at least one gas presence sensor providing an electrical output signal;
   an electronic processing circuit receiving the electrical output signal;
   at least one electronic memory of permanent type;
   a first communication line connecting the at least one electronic processing circuit to said electronic circuit;
   at least one warning device selected from a group comprising optical warning devices, acoustic warning devices, and warning devices providing both an optical and an acoustic alarm;
   a second communication line connecting the at least one warning device to the electronic circuit;
   at least one activator apparatus;
   a third communication line connecting the at least one activator apparatus to said electronic circuit;
   at least one logic gate;
   at least one bidirectional serial communication line connecting the electronic circuit to the at least one logic gate forming a serial communication output of the sensing device,
   wherein, while located in an environment of known gas concentration, the sensing device is put into a condition such that it can be calibrated, said condition being achieved at the moment in which, starting from a rest condition, power is supplied to the sensing device, and
   at least one external processor feeds a logic command from outside the sensing device to said logic gate by transmitting through said bidirectional serial communication line a plurality of parameters relating to the environment.

2. An electronic device as claimed in claim 1, wherein said parameters contain information relative to at least one of the gas concentration value set from the outside of said environment, the gas concentration value measured by said sensor, and the temperature and humidity of the air within the environment.

3. An electronic device as claimed in claim 2, wherein said electronic processing circuit is able to analyze the values of said parameters together with the gas concentration value measured by said sensor, and to construct a table of values corresponding to the difference between the gas concentration measured by said sensor and the gas concentration set from the outside as the gas concentration, temperature and humidity values of the environment set from the outside vary, said table of values being memorized within said permanent electronic memory.

4. An electronic device as claimed in claim 3, wherein said electronic processing circuit senses the gas concentration value measured by said sensor and corrects it on the basis of said memorized value table, to feed at least one command along said communication lines and along said bidirectional serial line for the purpose of one of activating the warning device, controlling said logic gate, and operating said actuator apparatus, in the case in which the corrected value of the gas concentration within the environment exceeds a predetermined threshold concentration.

5. An electronic device as claimed in claim 1, wherein said logic gate is driven as the serial output of an alarm state, there being associated therewith the at least one warning device.

6. An electronic device as claimed in claim 1, wherein said permanent electronic memory is a random access memory, constructed in accordance with one selected from EEPROM, FLASH EPROM, and buffered RAM technology.

7. An electronic device for sensing gas present in an environment, comprising:
   at least one gas presence sensor providing an electrical output signal;
   an electronic processing circuit receiving the electrical output signal;
   at least one electronic memory of permanent type;
   a first communication line connecting the at least one electronic processing circuit to said electronic circuit;
   at least one warning device selected from a group comprising optical warning devices, acoustic warning devices, and warning devices providing both an optical and an acoustic alarm;
   a second communication line connecting the at least one warning device to the electronic circuit;
   at least one activator apparatus;
   a third communication line connecting the at least one activator apparatus to said electronic circuit;
   at least one logic gate;
   at least one bidirectional serial communication line connecting the electronic circuit to the at least one logic gate forming a serial communication output of the sensing device;
   wherein, while located in an environment of known gas concentration, the sensing device is put into a condition such that it can be calibrated, said condition being achieved at the moment in which, starting from a rest condition, power is supplied to the sensing device;
   at least one external processor feeds a logic command from outside the sensing device to said logic gate by transmitting through said bidirectional serial communication line a plurality of parameters relating to the environment, wherein the sensing device is formed on an electronic printed circuit card, said printed circuit comprising a plurality of electronic cards, which are mounted on at least one terminal strip and are connected together by detachment lines for separating the cards, the electronic devices provided on said cards being connected together by a single printed conductor which connects the logic gates of each electronic device to a single external connection point, said external connection point being provided on said terminal strip.

* * * * *